US00PP16266P3

(12) United States Plant Patent
NeSmith et al.

(10) Patent No.: US PP16,266 P3
(45) Date of Patent: Feb. 21, 2006

(54) RABBITEYE BLUEBERRY PLANT NAMED 'ALAPAHA'

(50) Latin Name: *Vaccinium ashei*
Varietal Denomination: Alapaha

(75) Inventors: D. Scott NeSmith, Molena, GA (US); Arlen D. Draper, Payson, AZ (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 277 days.

(21) Appl. No.: 10/255,211

(22) Filed: Sep. 26, 2002

(65) Prior Publication Data

US 2004/0064863 P1 Apr. 1, 2004

(51) Int. Cl.
*A01H 5/00* (2006.01)

(52) U.S. Cl. ..... Plt./157

(58) Field of Classification Search ..... Plt./157
See application file for complete search history.

*Primary Examiner*—Anne Marie Grunberg
*Assistant Examiner*—June Hwu
(74) *Attorney, Agent, or Firm*—MacCord Mason PLLC

(57) ABSTRACT

The most distinctive feature of the rabbiteye blueberry, 'Alapaha', is its combination of early ripening and late flowering. This combination results in reduction of frost damage during flowering, with subsequent significant increases in productivity of high quality fruit over the current early varieties for Georgia.

1 Drawing Sheet

STATEMENT AS TO RIGHTS TO INVENTIONS MADE UNDER FEDERALLY-SPONSORED RESEARCH AND DEVELOPMENT

The invention was made in part with Federal funds pursuant to the Hatch Act.

BACKGROUND OF THE INVENTION

1. Field of the Invention

*Vaccinium ashei* Reade. (Rabbiteye blueberry) 'Alapaha'.

The fruit of the plant is primarily used as fresh fruit for shipping. Also suitable for customer-pick and processing markets.

2. Description of Relevant Prior Art

The new and distinct variety of rabbiteye blueberry was selected in 1972 at the Coastal Plain Experiment Station in Tifton, Ga. from a cross of T-65 (non-patented)×'Brightwell' (non-patented) made in 1971 in Beltsville, Md. The selection was subsequently evaluated for a number of years at the University of Georgia's Blueberry Research Farm near Alapaha, Ga. In 1992, the new variety was entered in the Southern Regional Blueberry Evaluation Trial, where it was tested at diverse locations including Alapaha, Ga., Clarksville, Ark. (location of the University of Arkansas' Fruit Substation Research Farm), and Poplarville, Miss. (location of the USDA-ARS Small Fruit Laboratory). Resulting data from 10-site/years indicate that the new variety is widely adapted to areas conducive to rabbiteye blueberry production.

The new variety has been asexually propagated on many occasions since 1972 by softwood cuttings. It roots readily from softwood cuttings and in all cases the clones propagated from cuttings have maintained the vegetative and fruit characteristics of the original selection.

The new variety has been primarily compared with the early season rabbiteye standard 'Climax' (non-patented). In Alapaha, Ga. and Clarksville, Ark., productivity of the new variety substantially exceeded that of 'Climax' in each trial year with the 4 year average yield being 64% greater than 'Climax' at Alapaha, and the 3 year average yield being 153% greater than 'Climax' at Clarksville and 23% greater than 'Climax' at Poplarville. Much of the increased production of the new variety is due to its later bloom time as compared to 'Climax', especially in south Georgia, which lessens the risk of spring freeze damage during bloom. The later bloom time of the new variety is not coupled with an equal delay in ripening, however, which would result in decreased fresh market value. Therefore, one of the greater attributes of the new variety is that it blooms at least a week after 'Climax', yet ripens before or within a few days of the standard cultivar.

The chill requirement of the new variety is estimated to be 450 to 550 hours below 7° C. This is derived from comparing the bloom date of the new variety following chilling to that of one of its parents 'Brightwell' and 'Climax' over a 3 year period. 'Climax' has a reported chill requirement of 450 to 500 hours, and 'Brightwell' has a reported requirement of 350 to 400 hours. The parent T-65 was a test selection that had earlier fruit ripening when compared to the new variety.

Fruit quality of the new variety and 'Climax' was determined by independent subjective ratings for each of 3 years in the Southern Region Blueberry Evaluation Trial. The berries were rated on a scale of 1=poorest to 10=best, with a value of 6 generally considered "commercially acceptable" for various characteristics including size, scar, color, firmness, and flavor. The 3-year average values for berry attributes from Georgia, Arkansas, and Mississippi are very similar, with ratings of 7 to 8. The only consistent difference across locations was that 'Climax' color was slightly better (more blue), although the new variety's color is commercially viable at 7.2 to 7.5.

The bush type of the new variety is very similar to one of its parents 'Brightwell'. It is vigorous, and upright, with a fairly narrow crown. The 3-year average plant vigor ratings from sites of the Southern Regional Trials are very similar for 'Climax' and the new variety. Leafing of the new variety appears to be better than 'Climax' (based on observations) even following mild winters. 'Climax' is known to be a poor leafing Cultivar, which causes problems with fruit set and sizing in some years. Thus, the new variety easily produces sufficient stems to "renew" the plant. Some twig die-back has been observed at Alapaha, but 4 years of observations have indicated this has caused no serious problems.

'Climax' is considered a standard cultivar by the Georgia industry with respect to mechanical harvesting rabbiteye fruit for the fresh market. In 1999, testing of mechanical harvesting of 'Climax' and the new variety were conducted at Alapaha, and the data suggested that the new variety would be suitable for mechanical harvesting, with fruit losses and firmness losses being similar to 'Climax'.

The new variety is self-fertile to a degree, similar to 'Brightwell'. However, it is recommended that the new variety be planted with another rabbiteye cultivar with a similar bloom time for cross pollination. The recent release 'Austin' (non-patented) would likely be a good choice for planting with the new variety. The cultivar Premier (non-patented) would be suitable as well. 'Climax' would likely be a poor choice for cross pollination in south Georgia, since the bloom times vary so much.

The new variety has been named the 'Alapaha' cultivar.

SUMMARY OF THE INVENTION

Description and specifications of a new and distinct rabbiteye blueberry named 'Alapaha' which originated from seed produced by a hand-pollinated cross of T-65 and 'Brightwell' is provided. The new 'Alapaha' variety can be distinguished by its short fruit development period, high and consistent productivity, moderate chill requirement, late bloom-early ripening, small berry scar, and high-quality fruit suitable for mechanical harvesting for the fresh market.

BRIEF DESCRIPTION OF PHOTOGRAPH

The accompanying photograph shows typical specimens of the fruit and leaf of 'Alapaha' in color as nearly true as it is reasonably possible to make a color illustration of this character.

BOTANICAL DESCRIPTION OF THE PLANT

The following is a detailed description of the botanical and pomological characteristics of the subject blueberry clone. Where dimensions, sizes, colors, and other characteristics are given, it is to be understood that such characteristics are approximations and averages set forth as accurately as practicable. Color data are presented in Royal Horticultural Society Colour Chart designations. Plant specimens used to describe the Alapaha cultivar were established in Alapaha, Ga. in 1992, and grown without supplemental irrigation. The descriptions and data described in this application come from mature plants more than seven years old.

Plant:

*Size.*—Medium: plants were 1.8 to 2.1 m tall with an average canopy width of 1.5 m after 10 years without pruning.

*Growth habit.*—Plants are semi-upright, with some spreading. Crowns are narrow, with 4 to 6 major trunks. The narrow crowns facilitate mechanical harvesting.

*Growth.*—Medium vigor. Plants have abundant twiggy growth each year, with only moderate cane growth. Some twig die-back occurs each year.

*Productivity.*—High and concentrated ripening; good consistency from year to year. In Alapaha, Ga. mature plants of the cultivar Alapaha yielded 13.1 lbs/bush/year on average over a 5 year period from 1998 to 2002, compared to only 7.4 lbs/bush/year for the "Climax" cultivar. In Clarksville, Ak. mature plants of the cultivar Alapaha yield 18.7 lbs/bush/year on average over a 3 year period from 1997 to 1999, compared to only 7.4 lbs/bush/year for the cultivar Climax.

*Cold hardiness.*—Similar to other rabbiteye blueberry cultivars such as 'Brightwell' and 'Climax'.

*Chilling requirement.*—Plant requires 450–550 hours of temperatures at or below 7° C. to induce normal leafing and flowering during the spring.

*Leafing.*—Plants readily break numerous leaf buds simultaneously with or just after anthesis.

*Canes.*—Mostly erect, with only moderate branching. Main cane base diameter (10 year old plant) 35 mm, color Greyed-Green (198C); first major branch diameter 25 mm, color Greyed-Green (198C); 2 year old cane diameter 12 mm, color Greyed-Orange (177B), some flaking of bark; current season wood diameter 3 mm, color Yellow-Green (144C).

*Fruiting wood.*—Numerous twigs 5 to 10 cm in length, with internode lengths of 10 to 12 mm.

*Disease resistance.*—Moderate twig die-back, but followed by adequate annual rejuvenation; some susceptibility to various defoliating leaf diseases; good tolerance to stem canker.

Foliage:

*Leaf color.*—Healthy mature leaves: top side of leaf Green (137A), under side of leaf Green (137C).

*Leaf shape.*—Elliptic.

*Leaf margins.*—Crenulate to serrulate.

*Leaf venation.*—Pinnate, with a slight arcuate pattern.

*Leaf apices.*—Broadly acute to acuminate.

*Leaf bases.*—Acute.

*Suckering.*—The Alapaha cultivar have only a slight tendency for suckering. The tendency would be considered average or below for Rabbiteye blueberries.

*Leaf dimensions.*—Length 60 to 7 mm; width 30 to 35 mm.

*Petioles.*—Leaves of the Alapaha cultivar have smooth, non-pubescent upper and lower surfaces. Petioles of a newly mature leaf are less than 2 mm in length and have a Green (147C) color. Leaves glabrous, except for stalked glands along leaf margins.

Flowers:

*Color.*—White (155D) when fully opened, some Red-Purple (58C) color on corrollas just prior to bloom opening.

*Date of 50% antehesis.*—March 16 (4 year average).

*Flower shape.*—Urecolate.

*Flower bud number.*—Medium to high.

*Flower per cluster.*—6 to 10, average 8.

*Flower fragrance.*—very little.

*Corolla.*—Corolla length is 8–10 mm, and the width is 4.8–5.2 mm. The corolla color is Green-White (157D), and the corolla aperature width is 2.0–2.4 mm.

*Flower peduncle.*—Length is 10–16 mm; color green (138B).

*Flower pedicle.*—Length 3.5–4.0 mm; color green (139C).

*Calyx (with sepals).*—diameter 5.0–6.0 mm; calyx color green (138A).

*Stamen.*—Length 7.0–9.0 mm; number/flower 10; filament color green-white (157A).

*Style.*—Length 9–10 mm; color yellow-green (145A).

*Pistil.*—Length 11–13 mm; ovary color yellow-green (146A).

*Anther.*—Length 4 mm; number 10; color greyed-orange (172A).

*Pollen.*—Abundance medium to high; pollen color yellow (11C). The cultivar has a small degree of self-compatibility.

Fruit:

*Date of 50% maturity.*—June 1 (4 year average).

*Fruit development period.*—78 days, 9 days shorter than the cultivar 'Climax'.

*Berry color.*—Medium blue (101B), with moderate surface wax.

*Berry size.*—Medium. First harvest average 1.35 g/berry, late season average 1.0 g/berry. Berries are 14 to 15 mm tall and 15 to 16 mm in diameter.

*Berry shape.*—Very rounded, nearly spherical.

*Fruit stem scar.*—Small, dry, little or no tearing.

*Berry color.*—With wax blue (101C); with wax removed black (202A).

*Berry flesh color.*—Green-white (157B).

*Berry surface wax abundance.*—medium to high.

*Berry size.*—Height from calyx to scar 12.5–13.5 mm; diameter 14.0–14.5 mm.

*Berry firmness.*—Good. Firmer than the cultivar 'Premier', but slightly less firm than 'Climax'.

*Berry flavor and texture.*—Flavor sweet with mild to moderate acid level. Skins and seeds normal for rabbiteye cultivars.

*Storage quality.*—Good.

*Suitability for mechanical harvesting.*—Good.

*Uses.*—Primarily used as fresh fruit for shipping. Also suitable for customer-pick and processing markets.

Seed:

*Seed color.*—greyed-orange (165B).

*Seed abundance in fruit.*—medium.

*Seed dry weight.*—55.6 mg/100.

*Seed size.*—1.60 to 1.80 mm long for fully developed seeds.

It is claimed:

1. A new and distinct variety of rabbiteye blueberry plant, substantially as illustrated and described, characterized by its early ripening and late flowering resulting in high productivity of high quality fruit.

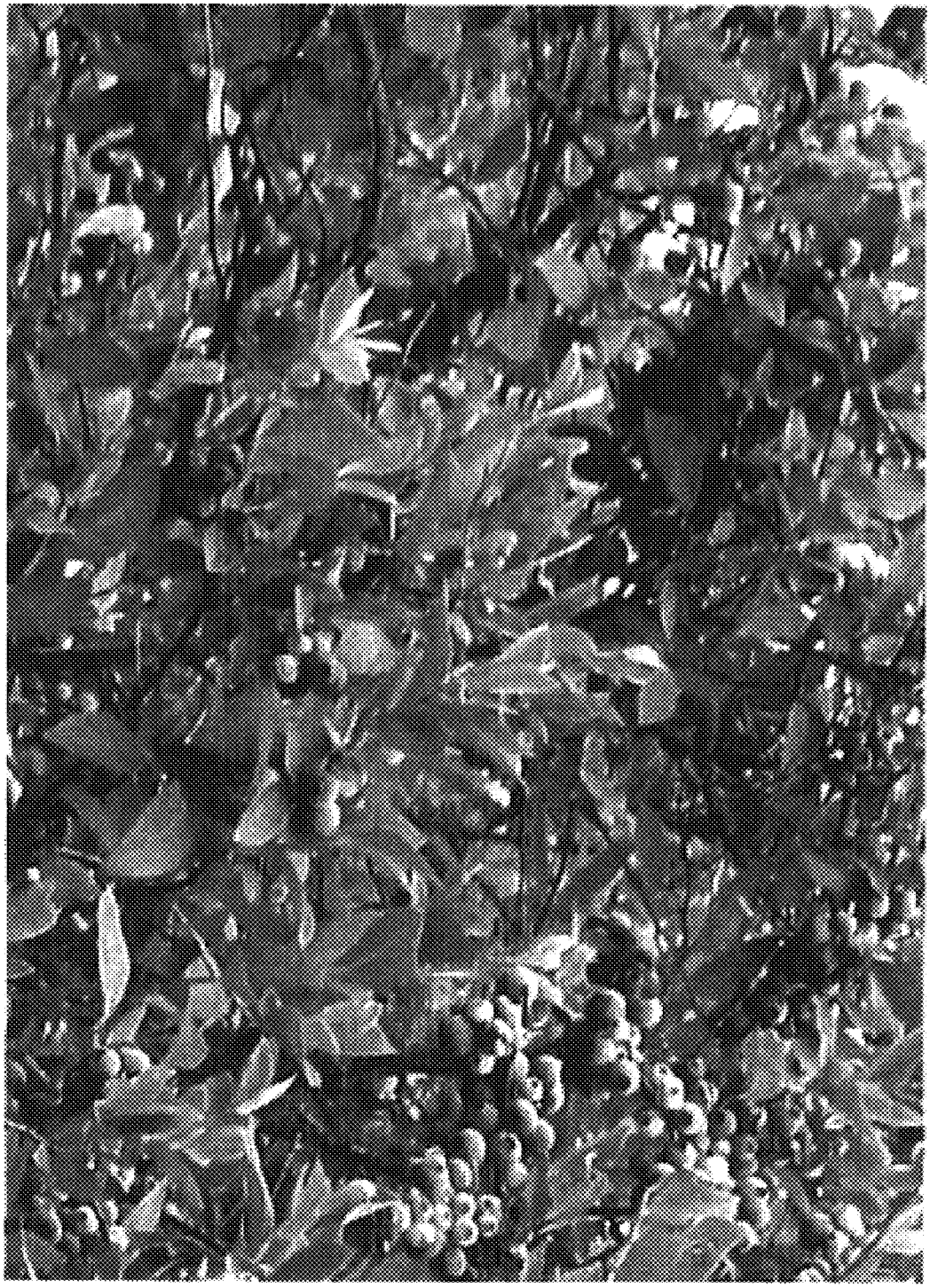

* * * * *